(12) United States Patent
Vasilenko

(10) Patent No.: US 10,201,172 B2
(45) Date of Patent: *Feb. 12, 2019

(54) METHOD AND DEVICE FOR DISINFECTION AND/OR PURIFICATION OF A PRODUCT

(71) Applicant: Vitabeam Ltd, London (GB)

(72) Inventor: Vladimir Vasilenko, Martintown (CA)

(73) Assignee: Vitabeam Ltd, London (GB)

( * ) Notice: Subject to any disclaimer, the term of this patent is extended or adjusted under 35 U.S.C. 154(b) by 43 days.

This patent is subject to a terminal disclaimer.

(21) Appl. No.: 15/267,336

(22) Filed: Sep. 16, 2016

(65) Prior Publication Data

US 2017/0000168 A1    Jan. 5, 2017

Related U.S. Application Data

(63) Continuation of application No. 13/265,650, filed on Dec. 20, 2011, which is a continuation of application (Continued)

(30) Foreign Application Priority Data

Apr. 21, 2009   (NL) ..................... 1036892

(51) Int. Cl.
| | | |
|---|---|---|
| *A23L 3/26* | (2006.01) | |
| *A23B 4/00* | (2006.01) | |
| *A23B 7/015* | (2006.01) | |
| *A61L 2/08* | (2006.01) | |
| *A23B 4/015* | (2006.01) | |
| *A61L 2/00* | (2006.01) | |
| *A61L 9/18* | (2006.01) | |
| *C02F 1/30* | (2006.01) | |

(52) U.S. Cl.
CPC ............. *A23L 3/26* (2013.01); *A23B 4/015* (2013.01); *A23B 7/015* (2013.01); *A61L 2/0058* (2013.01); *A61L 2/084* (2013.01); *A61L 2/085* (2013.01); *A61L 9/18* (2013.01); *C02F 1/30* (2013.01); *A23V 2002/00* (2013.01); *A61L 2202/11* (2013.01)

(58) Field of Classification Search
CPC ....................................... A23L 3/26
USPC ............................................... 422/22
See application file for complete search history.

(56) References Cited

U.S. PATENT DOCUMENTS 6,030,653 A * 2/2000 Rosenthal ............ A23B 4/015
                                                        422/24
2009/0177125 A1 * 7/2009 Pilcher ............ A46B 15/0034
                                                        601/18
(Continued)

FOREIGN PATENT DOCUMENTS

WO    WO-2004100684 A1 *  11/2004 ............ A01N 3/00

OTHER PUBLICATIONS

Luksiene et al., Prospects of photosensitization in control of pathogenic and harmful micro-organisms, Apr. 15, 2009, Journal of Applied Microbiology, 107, 1415-1424 (Year: 2009).*

*Primary Examiner* — Kevin Joyner
*Assistant Examiner* — Holly M Mull
(74) *Attorney, Agent, or Firm* — Berggren LLP

(57) ABSTRACT

The present invention relates to a method and device for illuminating and at the same time purifying or disinfecting products such as air, flowers, food, vegetables, meat, poultry or fish. The method comprises the use of IR emitting LED elements.

11 Claims, 4 Drawing Sheets

Related U.S. Application Data

No. 14/617,981, filed on Feb. 10, 2015, now Pat. No. 9,457,109.

(56) References Cited

U.S. PATENT DOCUMENTS

| | | | | |
|---|---|---|---|---|
| 2009/0280223 A1* | 11/2009 | Scott | ................ | A23B 4/015 426/237 |
| 2015/0151014 A1* | 6/2015 | Vasilenko | ............. | A23B 4/015 426/248 |

* cited by examiner

METHOD AND DEVICE FOR DISINFECTION AND/OR PURIFICATION OF A PRODUCT

PRIORITY CLAIM

This application is a continuing application of U.S. patent application Ser. No. 14/617,981 filed on Feb. 10, 2015 and claiming priority of U.S. Ser. No. 13/265,650 filed on Dec. 20, 2011 and claiming priority of PCT/EP2010/055276 filed on Apr. 21, 2010 and NL1036892 filed on Apr. 21, 2009. Each of these documents is incorporated herein by reference.

FIELD OF THE INVENTION

The present invention relates to a method and device for purification or disinfection of products using infrared light. In particular, it relates to the purification or disinfection of fresh produce, liquids, air and solids using infrared light.

BACKGROUND OF THE INVENTION

Purification methods using light, in particular UV light are known and accepted in industrial applications since long ago. For instance in sewage stations, it is known to purify spoiled water using UV light in the form of long tubes, e.g. included in racks that are lowered in a water stream for longitudinal passage of water. Another application for "exterior disinfecting" of produce products is known from patent publication U.S. 132,784.

Patent publication WO2005031881 indicates disinfecting such as for water purification may also be performed by (LED) lamps, the advantage being "an appreciably superior effectiveness" over "disinfecting lamps known today—2004–(TUV, HOK and DBD)". This invention uses UV light. Other types of disinfecting lamps are recently proposed through the use of infrared or near infrared light. One example, from U.S. Pat. No. 6,030,653, discloses the use of visible or infrared light for cold pasteurisation a food product. The visible or near infrared light illumination always has to be preceded by illumination with near infrared light to create an optical window. A method and device using LED for purification of water are known from the PURE RAY pdf publication "water purification" as available on www.globalwarmingsolutions.com. This publication teaches the use of infrared light for purification purposes as being a relatively low cost purification method. In order to realize this method, infrared light over a wavelength from 810 nm to about 1300 nm is emitted from a source located centrally within a coiled liquid transporting, transparent hose towards liquid to be purified. The source may be a LED, connected to a power source and AC/DC converter. Pulsation is not mentioned or suggested. Yet, a requirement to further technical development is simultaneously recognised in both the known method and device for executing the same. It is therefore an object of the present invention to arrive to a generally applicable, highly effective method using LED components in a functional and economic manner, preferably in a manner applicable both in water purification as well as in living tissue products like fresh produce, flowers, fish and the like.

DETAILED DESCRIPTION OF THE INVENTION

The present invention relates to a method for disinfecting or purifying a product. The method comprises illuminating a product with infrared light from one or more LEDs.

One advantage of the present invention is that products are illuminated and purified or disinfected at the same time. This is important at various locations, such as for example at retail shops for improved illumination of flowers and fresh produce which is installed for sale. Using the method or device according to the present invention, such display for sale is improved in quality because the colours of the product are reflected correctly and the life of freshness of the product is extended by the external and internal disinfection or purification.

A concomitant advantage is that freshness of products may be maintained at the work station, while maintaining and even improving the human vision at the work station in a safe way. This could not be achieved using UV light, which is damaging to the human eye, therefore not preferred in environments where humans are present. Yet another advantage is that using the method or device of the present invention, freshness may be maintained longer, not only in a conditioned environment, e.g. under cooled circumstances, but also outside a conditioned environment, due to the sanitary and respiratory impulse of elimination according to the present invention.

In the present context, the terms 'LED', 'LED element' and 'light emitting diode' are used interchangeably, and refer to light emitting diodes in all known forms, be it inorganic, organic, point-like or line-like. In one embodiment, the LEDs are wide angle elements, which refer to LEDs which deliver evenly distributed light rather than spotlights. In the present context, the phrase 'purifying or disinfecting a product' refers to the reduction of the number of microorganisms present on or in a product. In the present context, the terms 'infrared light' and 'IR light' are used interchangeably and refer to electromagnetic radiation of a wavelength in the range of about 700 to about 1000 nm.

In the present context, 'white light' refers to electromagnetic radiation which is visible to the human eye and which has a wavelength within the range of about 380 to about 800 nm. The term 'warm white light' refers to white light with a wavelength within the range of 425 nm to 475 nm, preferably with the peak of emission around 455-465 nm, The term 'cold white light' refers to white light with a wavelength within the range of about 500 nm to about 700 nm, with the peak of emission around 600 nm.

According to the method of the present invention, the product is illuminated by IR light emitted by one or more LED elements. In a preferred embodiment, the IR light emitted by the LED is of a wavelength within a range from 900 nm to 960 nm. Preferably, the light emitted by the IR LED element has a wavelength of 940 nm.

In another embodiment according to the invention, the product is illuminated by a combination of IR light and white light. The IR light and white light are typically emitted simultaneously and by separate LEDs. Preferably, the LEDs emitting white light comprise LEDs emitting cold white light and LEDs emitting warm white light. In a preferred embodiment, the product is illuminated by a set of LEDs comprising one or more LEDs emitting IR light of a wavelength within a range from 900 nm to 960 nm, one or more LEDs emitting warm white light with a wavelength within a range of 425 nm to 475 nm and one or more LEDs emitting cold white light with a wavelength within a range of 500 nm to 700 nm. More preferably, the product is illuminated by a set of LEDs comprising one or more LEDs emitting IR light with a wavelength of 940 nm to 950 nm, one or more LEDs emitting warm white light with a wavelength within a range of 455 to 465 nm and one or more LEDs emitting cold white light with a wavelength within a range of 600 to 620 nm. The LEDs may be used in high power output and may emit continuously or may be pulsating. If pulsating emission is used, pulsation is preferably with high frequency. The radiant output of the LEDs is preferably at least 10 mW, more preferably, it is at least 50 mW, at least 100 mW, at least 500 mW or at least 1 W. More preferably, the LEDs are high power LEDs with a radiant output of at least 5 W, at least 10 W, at least 15 W, at least 20 W, at least 25 W, at least 30 W, at least 35 W or at least 40 W, in pulsed or continuous mode. In one embodiment, the LEDs are high power LED elements with a light intensity of at least 500 mW/cm$^2$, at least 600 mW/cm$^2$, at least 700 mW/cm$^2$, at least 800 mW/cm$^2$, at least 900 mW/cm$^2$ or at least 1000 mW/cm$^2$, in pulsed or continuous mode. Preferably, high power LEDs deliver in pulsed mode at least 1.5 W/cm$^2$, at least 2.0 W/cm$^2$, at least 2.5 W/cm$^2$ or at least 3.0 W/cm$^2$. The power output of the LEDs may be adjusted in any convenient way. In one embodiment, the output is adjusted per type of specific wavelength.

The current feeding the LED elements may be continuous or pulsed. Preferably, the feed is pulsed, because this will have a stronger purifying or disinfecting effect. Most preferably, the feed is pulsed with a high frequency, which refers to a frequency in the range of 10 kHz to 1000 kHz. Preferably, the feed is pulsed at a frequency in the range of 100 kHz to 1000 kHz. More preferably, the feed is pulsed at a frequency in the range of 500 kHz to 1000 kHz.

The duty cycle of pulsation may vary. In one embodiment, the duty cycle of pulsation is 10% duty cycle and 10% power output. In another embodiment, the duty cycle of pulsation is 100% duty cycle and 100% power output. Several duty cycles may be combined. Therefore, in one embodiment, the duty cycle in a first setting is 100% duty cycle and 10% power output and in a second setting is 100% duty cycle and 100% power output.

All kinds of bacteria, both Gram positive and Gram negative, fungi or parasites may be combated using the method according to the present invention. Suitable examples include bacteria, yeast, fungi and parasites which belong to the genus, family or group *Escherichia, Lactobacillus, Legionella, Leuconostoc, Listeria, Pediococcus, Salmonella, Shigella, Staphylococcus, Vibrio, Yersinia, Aspergillus, Penicillium, Saccharomyces, Cryptosporidium, Giardia*. In particular the species or isolates referred to as *Escherichia coli, Listeria monocytogens, Salmonella typhi, Shigella dysenteriae, Staphylococcus aureus, Vibrio cholera, Yersinia enterocolitica* and *Giardia lambia*. Also ESBL-forming bacteria may be combated using the method according to the invention.

Without wishing to be bound by theory, the inventor suggests that the method according to the invention is particularly suitable to combat iron dependent bacteria, because it triggers a photoreceptor response mechanism in iron dependent bacteria, such as *E. coli, Salmonella, Listeria* and *Legionella*. This turns off a ferric uptake repressor which prevents aerobactin and specifically enterobactin from being synthesized, thereby inhibiting the assimilation of $Fe^2VFe^{3+}$ by the iron dependant bacterial pathogen, which kills them.

Any product which needs disinfection or purification may be subjected to the method according to the present invention, both organic and inorganic products, both gases, liquids and solids, both metal comprising and metal-free products. Suitable examples of such products include air, water, produce, food and plants. In particular, flowers, including cut flowers, and food, including vegetables, dairy products, grain products, meat and fish. Suitable examples of flowers include flowers such as roses, gerberas, tulips, lilies, chrysanthemums, orchids and gladiolus. Suitable examples of food include fruits, such as citrus fruits, stone fruits, in particular mango's, pears, apples, prunes, oranges, strawberries and bananas; dairy products, such as milk, cheese and butter; vegetables, such as sprouts, lettuce, cucumber, bananas, carrots and potatoes; grain products, such as maize, rice, wheat, barley, sorghum and oats; meat, such as beef, pork, lamb and poultry; fish, such as salmon and tuna. The invention is particularly suitable for disinfecting or purifying water sources or containers like sewage, drinking water, swimming pools, whirlpools and all applications where air from water damp can be inhaled for risk of *Legionella*, such as waste heat water supplies, water distribution networks, cooling towers, showers and Jacuzzi's. The method according to the invention can also be used to disinfect or purify animals, such as the ones which provide the meat and fish as mentioned above; fruit, flowers and plants before harvest to strengthen them and free them from microorganisms; surfaces, such as from working tables in shops and kitchens. In another aspect, the present invention relates to a device for applying the method according to the present invention in all its embodiments for all the products mentioned above. The device comprises IR LED elements and a power for the LED elements for the purification or disinfection of a product. At the same time, the product is also illuminated. The IR LED elements are LED elements which emit light within a range from 900 to 960 nm. Preferably, the LED elements are 940 nm LED elements.

In a preferred embodiment, the device further comprises white light LED elements, for use in combination with the IR LED elements. Preferably, the white light LED elements comprise warm white light LED elements and cold white light LED elements. In one embodiment, the white light LED elements comprise a 3000 K LED element. In another embodiment, the white light LED elements comprise a 6500 K LED element. The IR LED elements and the white light LED elements may be arranged in any convenient way. In one embodiment, they are arranged in an alternating manner, i.e. an IR LED element is next to a white light LED element.

The number of IR LED elements and the number of white light LED elements in the device may vary depending on the form of the device and the application for which they are used. In one embodiment, the number of white light LED elements is larger than the number of IR LED elements.

The ratio of warm white light LED elements to cold white light LED elements may also vary depending on the application and the form of the device. In one embodiment, the number of cold white light LED elements is larger than the number of warm white light elements.

The device comprising the LED elements may have any suitable form. In one embodiment, the device has an elongated form and the LED elements are arranged in an elongated panel or string. The device may be used in a system for purifying or disinfecting a product, as mentioned in the method according to the invention, in all its embodiments and for all the products mentioned above.

Therefore, a system for purification of a product comprising an LED light source for emitting IR light onto the product is also part of the present invention. The IR light source is typically separated from the product. This may be done, for example, by a glass or synthetic material which is transparent for IR light. The LED light source may be included in a holder. In one embodiment, the LED light source is included in an elongated holder for a multiplicity of LED elements.

The product is preferably guided by a guide element. If the holder of the LED source is elongated, the guide element preferably stretches in the direction of elongation of said light source. Holder and guide element may be attached to each other. In one embodiment, the guide element is a tube, for example a PVC tube.

The LED source in the system according to the invention may be positioned in any suitable way. In one embodiment, the LED source is at opposite sites of the guiding element. Preferably, it is at two opposite sites of the guiding element, for example, above and below, or left and right. In one embodiment, the system further comprises a LED light source for emitting white light in combination with the IR light.

The system according to the present invention may be applied in various applications, including all the applications mentioned before for the method. In particular, in refrigerators for professional and domestic use, purification of air, swimming pool purification, household application and for purification of shower water. Of more particular interest are applications where air from damp water can be inhaled for risk of *Legionella*, such as waste heat water supplies, water distribution networks, cooling towers, showers and Jacuzzi's.

In applications involving a pool of liquid, such as a swimming pool, or tubs as may be used on bathroom showers, a bypass system may be provided including a pump for the purpose of letting pass a fraction of the amount of liquid in said pool per unit of time, so as to maintain a proper sanitary level in said pool, in particular to the extent that the addition of chemicals like chloric is not at all or to a significantly lowered level required.

EXAMPLES

Example 1 System According to the Invention

Figure 1:
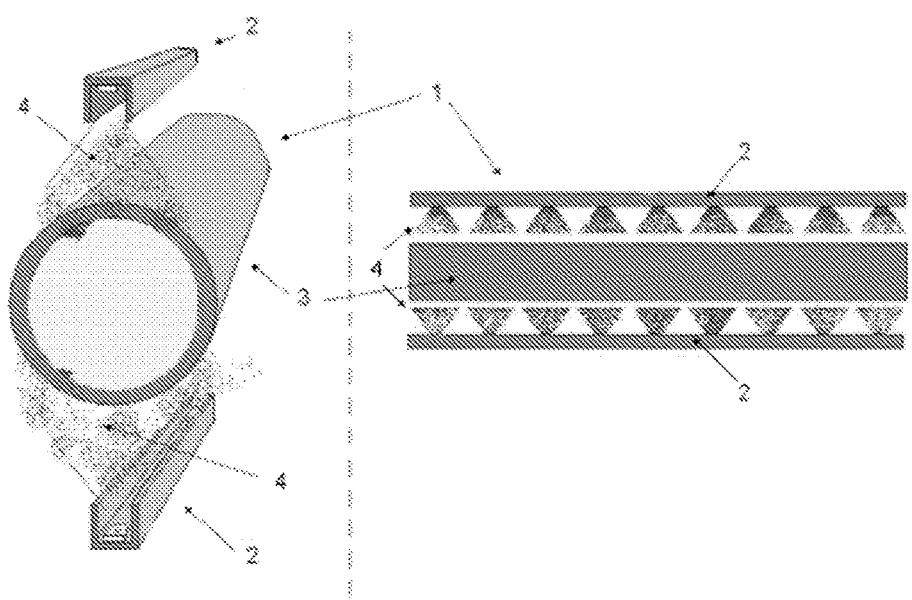
FIG. 1 is an example of a new device applying a new method of IR purification using LED as a light source.

FIG. 1 illustrates a disinfection system (1) in accordance with the present invention. A string of IR and warm and cold white light LEDs comprised in a casing form a lamp (2). Their radiation (4) illuminates and disinfects the contents of a transparent tube (3), in this example in the form of a PVC tube. The string of LED's stretches in the longitudinal direction of the tube over the projected axis of the tube. Two lamps (2) are here included at opposite sides of a tube (3) in the system.

Example 2 Device According to the Invention

Figure 2:
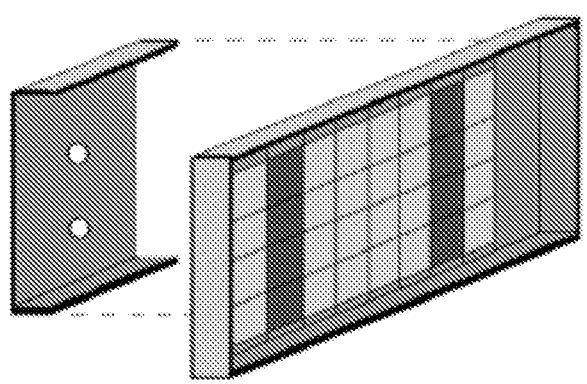
FIG. 2 exemplifies both part of said new device according to FIG. 1 and the new method of applying IR light for the purpose of purification.

FIG. 2 illustrates a lamp with considerable expansion of the LED's width wise of the lamp. This lamp could also be used in the application of FIG. 1, however is typically intended for applications like preserving fresh produce, flowers and the like. It is as well suited for use in sewage stations where the lamp, rather than being immersed in a stream of water, may be hung over such stream, either or not protected by an in between included screen, e.g. of glass or PVC.

The lamp includes IR LEDs separated by white light LEDs. In this example, the IR LEDs are directly flanked by so called cold white light LEDs. The lamp according to the invention may easily be incorporated in existing situations, e.g. for preserving food, in that the height thereof is very limited, in the order of typical measurements of LED, whereas length and width may be dimensioned in accordance with the disinfecting power required for the application.

The LEDs panel receives power from an electronic panel which allows to vary the power output of the LED light.

Example 3 Flower Treatment

Figure 3A:
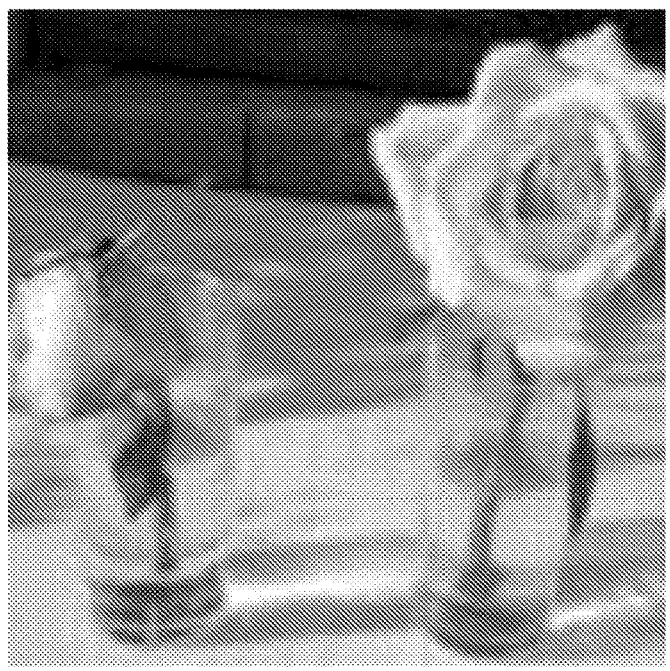
FIG. 3 A, B, C shows Gerberas and roses treated according to the method of the invention. Flowers treated according to the method of the invention are on the right and controls are on the left.
Figure 3B:
Figure 3C:

Gerberas and roses were treated according to the method of the invention. They were illuminated 8 hours per day. The illumination was a combination of LEDs emitting IR light (940 nm), white light (460 nm) and white light (600 nm). Pulsed light with a pulsation frequency of 600 kHz was used. As a control, gerberas and roses were illuminated with fluorescent light for 8 hours per day. The test continued 24 days. The results are shown in FIG. 3 A-C. Controls are always on the left.

What is claimed is:

1. A method for reducing the number of microorganisms in or on a product selected from cut-flowers, food, vegetables, meat, poultry, or fish, said method consisting of the steps of:
   a) providing a device having one or more LED elements, and a power for the LED elements, wherein the one or more LED elements emit IR light of a wavelength within a range of 930 to 960 nm, and a radiant output of at least 10 mW; and
   b) illuminating the product with the emitted wavelengths.

2. The method of claim 1, wherein the microorganisms are selected from the group consisting of bacteria, molds, yeasts and parasites.

3. The method of claim 2, wherein the microorganisms belong to group of *Escherichia, Legionella, Listeria, Aspergillus, Penicillium, Saccharomyces, Leuconostoc, Lactobacillus, Pediococcus, Staphylococcus, Salmonella, Shigella, Vibrio* or *Yersinia*.

4. The method of claim 1, wherein current feeding to the LED elements is pulsed at frequency in the range of 10 kHz to 1 MHz.

5. The method of claim 1, wherein the LED elements are separated from the product by a glass or synthetic material transparent for IR light, wherein LED sources are included in an elongated holder for multiplicity of LED elements, and wherein the product is guided by a product guide element stretching in the direction of elongation of the light source.

6. The method of claim 1, wherein step b) is conducted at room temperature or refrigerator temperature.

7. A method to reduce the number of microorganisms in or on a product selected from cut-flowers, food, vegetables, meat, poultry, or fish, said method consisting of steps of:
   a) providing a device comprising a multitude of LED elements, and a power for the LED elements, wherein at least one of the multitude of LED elements emits IR light of a wavelength within a range of 930 to 960 nm, at least one of the multitude of LED elements emits visible light of a wavelength within a range of 600-620 nm, more than one of the multitude of LED elements emit visible light of a wavelength within a range of 425-465 nm, such that the number of LED elements emitting light of 425 to 465 nm is larger than the number of LED elements emitting light of 600-620 nm, and b) illuminating the product simultaneously with the IR light and the visible light emitted by the LED elements of the device.

8. The method of claim 7, wherein radiant output of the LED elements is at least 10 mW.

9. The method of claim 7, wherein current feeding to the LED elements is pulsed at frequency in the range of 10 kHz to 1 MHz.

10. The method of claim 7, wherein the LED elements are separated from the product by a glass or synthetic material transparent for IR light, wherein LED sources are included in an elongated holder for multiplicity of LED elements, and wherein the product is guided by a product guide element stretching in the direction of elongation of the light source.

11. The method of claim 7, wherein step b) is conducted at room temperature or refrigerator temperature.

* * * * *

UNITED STATES PATENT AND TRADEMARK OFFICE
CERTIFICATE OF CORRECTION

PATENT NO. : 10,201,172 B2  
APPLICATION NO. : 15/267336  
DATED : February 12, 2019  
INVENTOR(S) : Vladimir Vasilenko Page 1 of 1

It is certified that error appears in the above-identified patent and that said Letters Patent is hereby corrected as shown below:

Please replace (63) with the following text below:
"This application is a continuing application of U.S. patent application Ser. No. 14/617,981 filed on Feb. 10, 2015, which is a continuing application of U.S. patent application of Ser. No. 13/265,650 filed on Dec. 20, 2011 and claiming priority of PCT/EP2010/055276 filed on Apr. 21, 2010 and NL1036892 filed on Apr. 21, 2009. Each of these documents is incorporated herein by reference."

Signed and Sealed this  
Seventh Day of May, 2019

Andrei Iancu  
*Director of the United States Patent and Trademark Office*